United States Patent [19]

Howard

[11] Patent Number: 5,809,825
[45] Date of Patent: Sep. 22, 1998

[54] SAMPLING DEVICE FOR AERATED LIQUIDS

[75] Inventor: Colin James Howard, Hornsby, Australia

[73] Assignee: Oscillation Pty Limited,, New South Wales, Australia

[21] Appl. No.: 615,118

[22] Filed: Mar. 13, 1996

[30] Foreign Application Priority Data

Mar. 15, 1995 [AU] Australia .................................. PN1770

[51] Int. Cl.$^6$ ............................. G01N 15/04; G01N 1/14; B01D 21/30
[52] U.S. Cl. ....................... 73/61.65; 73/61.68; 73/61.69; 73/864.35; 73/864.81
[58] Field of Search ................................ 73/61.65, 61.68, 73/61.69, 64.56, 864.34, 864.35, 864.81

[56] References Cited

U.S. PATENT DOCUMENTS

| | | | |
|---|---|---|---|
| 3,880,011 | 4/1975 | Johnson | 73/864.35 |
| 3,915,011 | 10/1975 | Nelson | 73/864.35 |
| 4,194,391 | 3/1980 | Rosenberger | 73/61.64 |
| 4,313,340 | 2/1982 | Schniewind | 73/61.69 |
| 4,318,296 | 3/1982 | Parker et al. | 73/61.69 |
| 5,431,037 | 7/1995 | Howard | 73/61.69 |

FOREIGN PATENT DOCUMENTS

| | | | |
|---|---|---|---|
| 60691 | 11/1994 | Australia | 73/61.65 |
| 1129676 | 8/1982 | Canada . | |
| 245806 | 11/1991 | Japan . | |

*Primary Examiner*—Hezron E. Williams
*Assistant Examiner*—Daniel S. Larkin
*Attorney, Agent, or Firm*—Michael J. Striker

[57] ABSTRACT

A device for the determination of the rate of sedimentation of particles in a sample of a liquid and controlling the addition of a flocculant to the liquid in accordance with the rate of sedimentation so determined. The device comprises a sample container (18), a sample inlet duct (17) in fluid communication with the sample container (18) and extending downwardly from a lower end thereof and adapted to extend into a body of liquid to be sampled, a suction unit (34) in fluid communication with an upper end of the sample container (18) and adapted to create a reduced pressure in the sample container such that a sample of the liquid is drawn into the sample container. Units (not shown) are provided to measure the rate of sedimentation of particles in the liquid sample and flocculant addition units (not shown) are adapted to add flocculant to the body of liquid from which the sample was drawn. Units (not shown) are provided to control the addition of flocculant from the flocculant addition units into the body of liquid in accordance with the rate of sedimentation of the particles in the liquid sample. The device is characterized in that the sample inlet duct (17) includes an S-bend (40) having a lower bight portion (46) below a lower end of the sample container (18) and an upper bight portion (47) adjacent to or above the upper end of the sample container (18). A gas inlet duct (45) is provided in communication with the sample inlet duct (17). Valve units (48) in the gas inlet duct (45) control the flow of gas through the duct (45). The valve units (48) are disposed at a level adjacent to or above the upper end of the sample container (18), and control units (not shown) are provided to control the opening and closing of the valve units (48).

7 Claims, 2 Drawing Sheets

SAMPLING DEVICE FOR AERATED LIQUIDS

FIELD OF THE INVENTION

The present invention relates to a device and method for the determination of the rate of sedimentation of particles in a sample of a liquid and controlling the addition of a flocculant to a body of the liquid from which the sample was drawn in accordance with the sedimentation rate so determined.

BACKGROUND ART

There are many occasions in the mining industry, in agriculture, and in waste water treatment when it is necessary to separate fine particulate matter from a body of a liquid such as water. This is often achieved by a process of sedimentation or settling. The rate of sedimentation of particles is partly dependent upon their mass and it is therefore advantageous in many cases to add a flocculant to the body of water to induce the fine particles to aggregate or floc together. This increases the mass of the particles and hence their sedimentation rate. As flocculant chemicals are expensive and as there may be adverse environmental effects from excessive flocculant addition, it is desirable to add only sufficient flocculant to the body of liquid to impart the desired rate of sedimentation to the particles in the liquid.

It is known to periodically measure the sedimentation rate of particles in a body of a liquid and to control the rate of addition of the flocculant to the body of liquid in accordance with the rate of sedimentation of the particles. If the particles are not sedimenting fast enough then more flocculant is added. If the particles are settling faster than is required then the addition of flocculant may be slowed down or stopped.

In known devices for the above purpose a sample of the liquid is drawn up into a sample container by the induction of a reduced pressure in the sample container. Once the liquid level in the container has reached a desired level a pinch valve in the lower end of the sample tube is closed and the vacuum applied to the sample container is released. The pinch valve serves to hold the liquid level constant in the sample container until the rate of sedimentation of the particles in the liquid has been determined. The pinch valve is then opened to release the sample from the sample container and to allow it to flow back into the body of the liquid.

Australian Patent Specification 60691/94 describes slurry suspension sampling equipment in which the liquid sample is drawn into a sample chamber and temporarily held at a predetermined level, to allow for the measurement of the settling rate of the suspension by a timer means which measures the actual settling period of the suspension between two predetermined levels, merely by the use of a vacuum applied above the sample. After the determination of the settling rate and the consequent adjustment of the flocculent flow control valve, the sample of liquid is discharged from the settling chamber via a discharge pipe located at the lower end of the settling chamber and which is normally held closed by a solenoid operated valve.

In some applications, the sample liquid will have been aerated as a result of stirring or mixing of the liquid. The gases in the liquid will tend to accumulate as bubbles on the flocculated particles in the sample and cause the particles to be more buoyant, and it has been observed that a proportion of the flocculated particles with attached gas bubbles will settle very slowly, remain suspended, or even slowly rise in the sample while there is an applied vacuum above the sample. This can have a serious effect of the accuracy of the measurement and/or the operation of the system.

It would therefore be desirable to provide a means of maintaining the level of the sample in the sample container without maintaining a reduced pressure above the sample and without having to resort to the mechanical valve means and its attendant problems.

DISCLOSURE OF THE INVENTION

The present invention consists in a device for the determination of the rate of sedimentation of particles in a sample of a liquid and controlling the addition of a flocculant to the liquid in accordance with the rate of sedimentation so determined, the device comprising a sample container, an inlet duct in fluid communication with the sample container and extending downwardly from a lower end thereof and adapted to extend into a body of liquid to be sampled, suction means in fluid communication with an upper end of the sample container and adapted to create a reduced pressure in the sample container such that a sample of the liquid is drawn into the sample container, means to measure a parameter indicative of the rate of sedimentation of particles in the liquid sample, flocculant addition means adapted to add flocculant to the body of liquid from which the sample was drawn and means adapted to control the addition of flocculant from the flocculant addition means into the body of liquid in accordance with the rate of sedimentation of the particles in the liquid sample, the device being characterized in that the inlet duct includes an S-bend having a lower bight portion below a lower end of the sample container and an upper bight portion adjacent to or above the upper end of the sample container, a gas inlet duct in communication with the inlet duct, valve means in the gas inlet duct to control the flow of gas through the duct, said valve means being disposed at a level adjacent to or above the upper end of the sample container, and control means to control the opening and closing of the valve means.

In a further aspect the present invention consists in a process for controlling the sedimentation of particles in a body of a liquid, said process comprising the steps of: drawing a sample of the liquid into a sample container having an upper end, and a lower end, through an inlet duct in fluid communication with the lower end of the sample container and with the body of liquid by producing a reduced pressure in the sample container, the inlet duct including an S-bend having a lower bight portion below the lower end of the sample container and an upper bight portion adjacent to or above the upper end of the sample container; opening a valve means on a gas inlet duct communicating with the S-bend to allow a gas to flow into the upper bight portion; releasing the reduced pressure in the sample container;

determining a parameter indicative of the rate of sedimentation of particles in the sample; controlling the addition of flocculants from a flocculant addition means into the body of the liquid in accordance with the rate of sedimentation of the particles in the sample; and retaining the sample in the sample container throughout the determining of the sedimentation rate of the particles in the sample by maintaining a balance between the liquid in the sample container and the liquid remaining in the S-bend after the valve means have been opened.

The device and process according to the invention may be applied to controlling the clarification of water in a wide range of industries including mining, agriculture and sewage treatment. It is particularly useful in coal washeries in which coal washwater is admitted to a thickener to induce settlement of the very fine coal and gangue particles entrained in the washwater. Once it has been clarified the washwater may be recycled through the coal washery while the fines settled out of the washwater are disposed of into tailing dams or stockpiles.

The measurement of the rate of sedimentation of the particles may be carried out by any suitable means known in the art. One suitable means includes a light disposed on one side of the sample container and a photoelectric cell disposed in the path of the light on the other side of the sample container. A timer is actuated as soon as a sample reaches a desired level in the sample container and is stopped when the particles in the container have settled to a level which allows the light to pass through the container and the liquid therein sufficiently to be registered by the photoelectric cell. The rate of addition of the flocculant to the body of the liquid is controlled in accordance with an algorithm based on the time recorded on the timer.

The suction means may comprise an air pump or a venturi vacuum generator which creates a reduced pressure in the sample container by pumping air therefrom and is electronically controlled. It could however comprise a mechanical piston adapted to move in a cylinder in fluid communication with the sample container to control the air pressure therein.

The suction means and the sample container must be so constructed that the reduced pressure in the sample container above the sample may be produced to draw the sample into the container up to a predetermined level, and then released when the valve means in the gas duct is opened so as to create a balanced condition such that the level in the sample container remains constant throughout the determination of the sedimentation rate.

BRIEF DESCRIPTION OF THE DRAWINGS

Hereinafter given by way of example only is a preferred embodiment of the invention describe with reference to the accompanying drawings in which.

BEST MODE OF CARRYING OUT THE INVENTION

Figure 1:
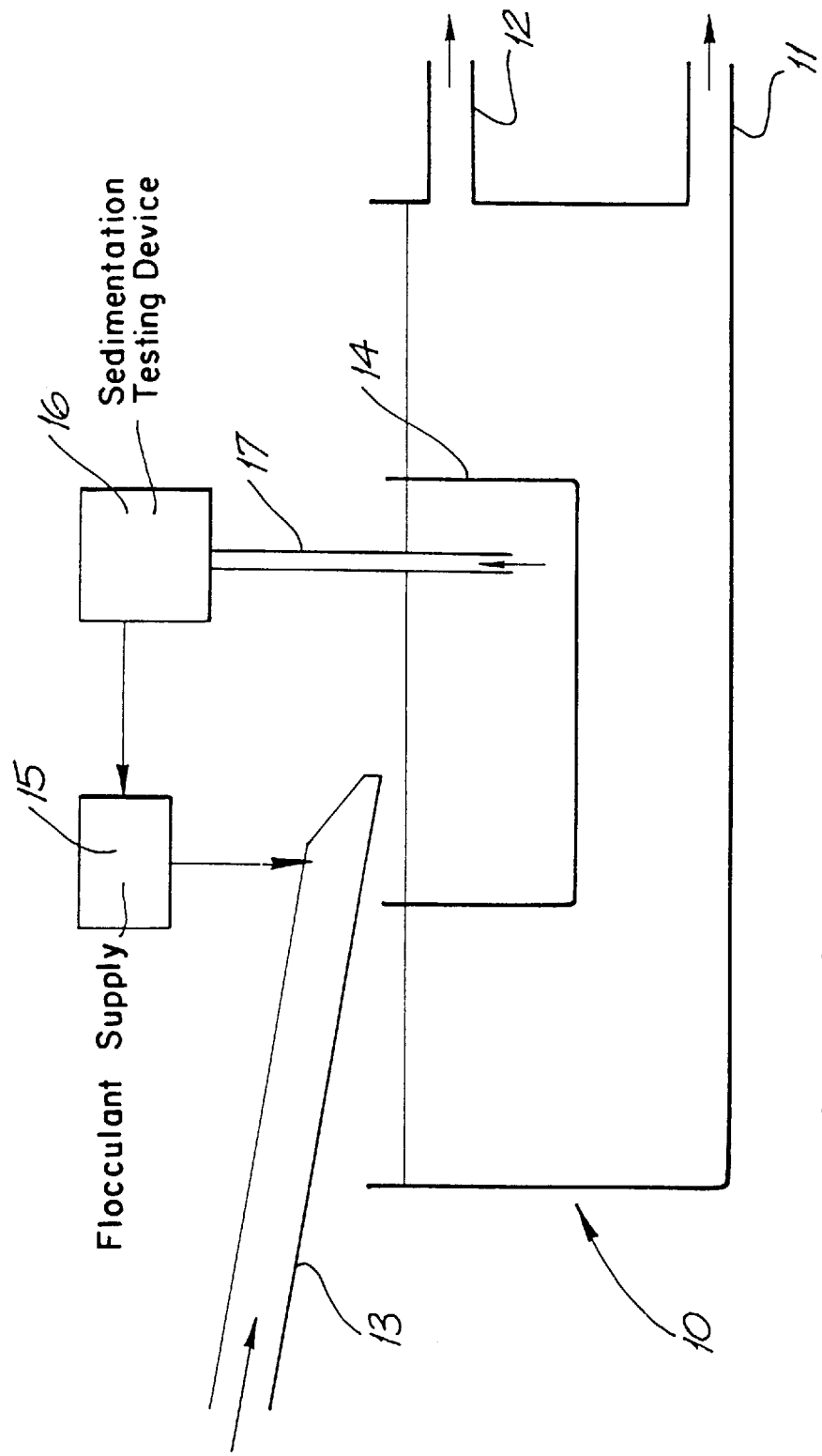
FIG. 1 is a diagrammatic presentation of a coal washery thickener fitted with a device according to the present invention.

As is shown in FIG. 1 a coal washery thickener includes a tank 10 having a lower outlet 11 for particulate slurry underflow and an upper outlet 12 for clean water overflow. Dirty washwater is delivered through a chute 13 into a central well 14 disposed in the middle of the tank 10. The dirty washwater contains fine particles of coal and gangue which may be clay or sand. A flocculant is metered into chute 13 from a flocculant supply device 15 to mix with the coal washwater. The flocculant causes the particulate matter in the washwater to flocculate and settle in the thickener. The clarified water is drawn from the tank 10 through upper outlet 12 and recycled through the coal washery. The settled flocculated particulate material is drawn out of the thickener through the lower outlet 11.

Figure 2:
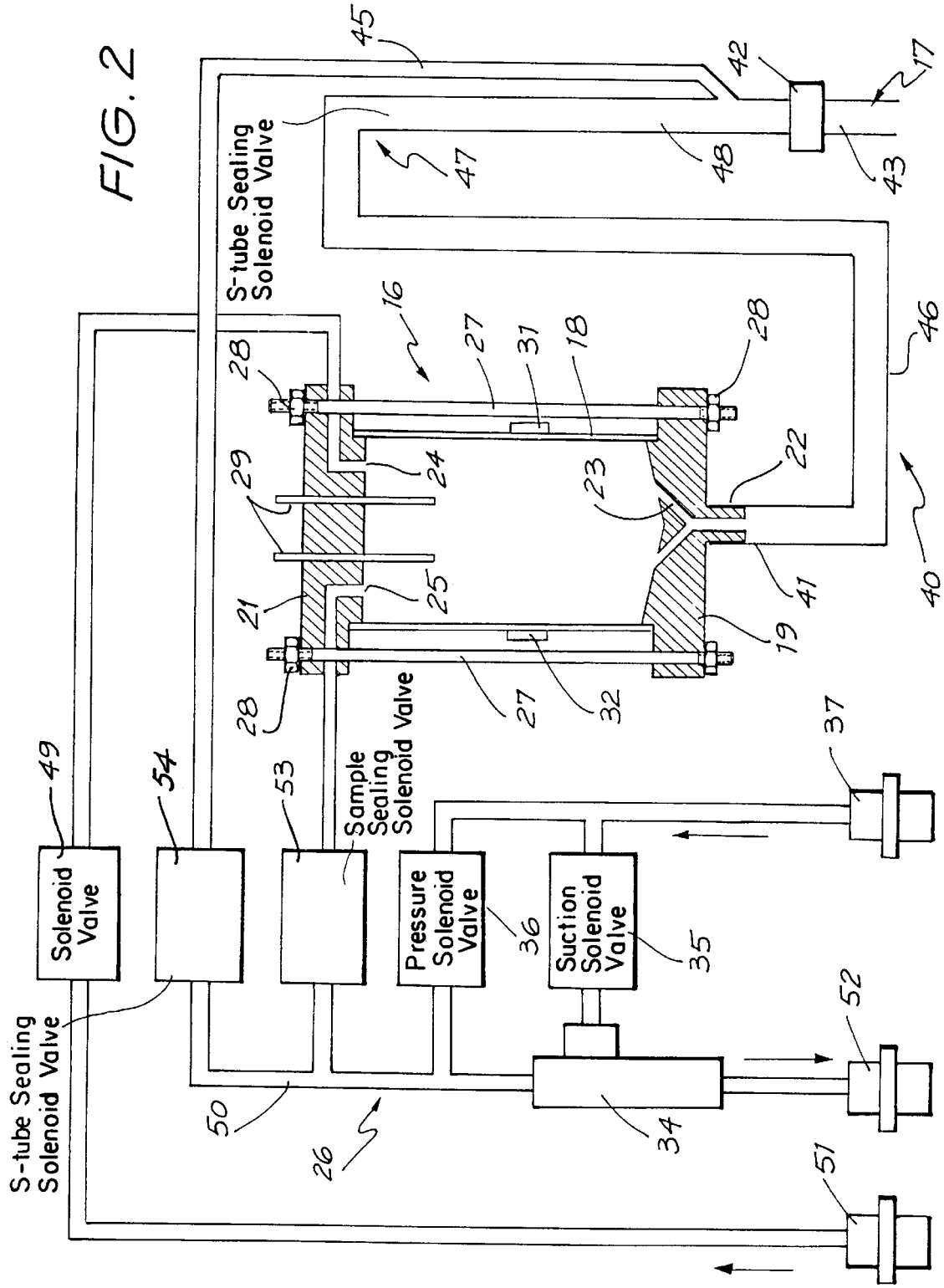
FIG. 2 is a diagrammatic representation of the sample container and associated suction means and S-bend suction pipe of the device according to the present invention shown in FIG. 1.

The addition of flocculant from the flocculant supply device 15 is controlled by a sedimentation testing device 16 shown in detail in FIG. 2. The device 16 peroidically draws a sample of the washwater from the centre well 14 of the thickener 10 through an inlet tube 17 which extends downwardly from the device 16 into the washwater. The rate of sedimentation of the particulate matter in the washwater is determined, as will be hereinafter described in more detail, and this data is used in an electronic control circuit of an electronic controller 60, which includes a sofware controlled micro-processor, to provide a signal for the flocculant supply device 15. In this way sufficient flocculant is added to induce effective flocculation and settlement of the particulate matter in the washwater while avoiding the use of the excessive amounts of flocculant.

The sedimentation device 16 comprises a glass sample receiving cylinder 18 having a lower end plate 19 sealingly engaged with its lower end and an upper end plate 21 sealingly engaged with its upper end. The lower end plate 19 is formed with a spigot 22 to which one end 41 of an S-bend section 40 of the inlet tube 17 is connected. The other end 42 of the S-bend section 40 is in turn connected to the straight vertical section 43 of the inlet tube 17.

The inlet tube 17 is in fluid communication with the interior of the sample receiving cylinder 18 through a Y-shaped bore 23. The lower single arm of the bore 23 opens into its diverging upper arms so that if liquid is drawn rapidly into the sample cylinder it will splash against the wall of the cylinder 18 rather than spray up against the underside of the upper end plate 21 which, as will be explained subsequently, carries height probes the operation of which could be disrupted if they were sprayed with inflowing sample liquid.

The upper end plate 21 includes a clean water inlet duct 24 connected via solenoid value 49 to a clean water supply 51 so that the inside of the sample receiving cylinder can be washed after each sampling cycle. It also includes an air passage 25 connected to an air pressure regulating circuit 26. The upper and lower end plates 21 and 19 are held in position on the ends of the sample receiving cylinder 18 by clamping rods 27 and corresponding locking nuts 28 spaced around the periphery of the cylinder 18.

A pair of height probes 29 extend downwardly through the upper end plate 21 into the interior of the sample receiving cylinder 18. The probes 29 are height adjustable relative to the cylinder 18 so that the operator can selectively adjust the height of the sample in the cylinder 18 at which the probes 29 will be bridged by the sample. A light 31 is positioned on the outside of the cylinder 18 and is arranged to direct a beam of light through the cylinder 18 towards photoelectric cell 32 positioned on a diametrically opposite side of the cylinder 18.

The air pressure regulating circuit 26 includes a venturi vacuum generator 34 connected to an exhaust port 52, a suction solenoid valve 35, a pressure solenoid valve 36 in parallel with the suction solenoid valve 35, and a compressed air supply 37. A sample sealing solenoid valve 53 is provided between a common pressure and suction line 50 and the sample receiving cylinder 18.

The S-bend section 40 has a first bight portion 46 below the level of the bottom end of the sedimentation device 16 and an upper bight portion 47 at or slightly above the upper end of the cylinder 18 so as to be slightly above the level of the lower ends of the probes 29 in the sedimentation device 16. The level of the upper bight portion 47 is set so as to maximize the height of the sample in the cylinder 18.

The lower end of a gas duct 45 is connected to the vertical section 48 of the S-bend section 40, at approximately the level of the bottom end of the sedimentation device. The gas duct 45 extends generally vertically upwards to a level at or slightly above the height of the top of the upper bight portion and is then connected to the circuit 26.

In operation a sampling cycle commences with the suction solenoid valve 35 closed and both the S-tube sealing solenoid valve 58 and the sample sealing solenoid valve 53 open. The pressure solenoid valve 36 is then opened allowing pressurised air from air inlet 37 to flow through both the gas duct 45 and the sample cylinder 18. This has the effect of purging any liquid from the S-tube 40 and the inlet tube 17.

The pressure solenoid valve 36 and the S-tube sealing solenoid valve 58 are then closed. The suction solenoid valve 35 is opened. This directs pressurised air through the venturi suction generator 34 causing a reduced pressure to develop in the common pressure and suction line 50, and thus in the sample cylinder 18, S-tube 40 and inlet tube 17. A fresh sample is thus drawn up the inlet tube 17, through the S-tube 40 and into the sample cylinder 18.

When the sample reaches the probes 29 a signal is generated that has a number of effects. Firstly the signal starts a timer. Secondly the signal causes the suction solenoid valve 35 to close thereby stopping the vacuum generator 34 from operating. The sample sealing solenoid valve 53 remains open for a short time as ambient air flows in the reverse direction through the vacuum generator 34 due to the reduced pressure in the sample cylinder 18 and is then closed. As the sample sealing solenoid valve 53 closes, the S-tube sealing solenoid valve 58 opens. This allows ambient air to flow through vacuum generator 34, common line 50 and the gas duct 45. The siphon effect in the S-tube is thus broken and the sample below the upper part of the upper bend 47 is discharged from the inlet tube. When this process is completed, the S-tube sealing solenoid 58 is closed and the sample sealing solenoid 53 is opened. The pressure in the sample cylinder 18 above the sample then reverts to atmospheric and the sample is maintained in the cylinder 18 by the weight of the balancing column of sample in the lower bight of the S-tube 40.

The particulate material in the sample in the cylinder 18 renders the liquid sample opaque. The beam from light 31 is therefore not registered by the photoelectric cell 32. As the particulates in the liquid sample settle, the upper level of the opaque particles drops below the light 31. The beam from the light 31 then strikes the photoelectric cell 32 which in turn stops the timer 59. The electronic control circuit of the electronic controller 60 uses this time in an algorithm to produce an output signal from a control signal generator 62 to the flocculant supply device 15 which responds by either increasing or decreasing the quantity of flocculant entering the dirty washwater in chute 13.

A predetermined time after the photoelectric cell 32 has been actuated the value controller 61 opens the pressure solenoid valve 36 and the S-tube sealing solenoid valve 58 to purge the old sample from the cylinder 18. While those valves are open a flow of clean water through duct 24 is then briefly introduced to clean the cylinder 18. This acts to purge the remnants of the sample and the washing liquid from the cylinder 18, the S-shaped tube 40, and the gas duct 45. The cycle is then completed.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A device for the determination of the rate of sedimentation particles in a sample of a liquid and controlling the addition of a flocculent to the liquid in accordance with the rate of sedimentation so determined, the device comprising a sample container, a sample inlet duct in fluid communication with the sample container and extending downwardly from a lower end thereof and adapted to extend into a body of liquid to be sampled, a vacuum generator in fluid communication with an upper end of the sample container and adapted to create a reduced pressure in the sample container such that a sample of the liquid is drawn into the sample container through the sample inlet duct, means to measure a parameter indicative of the rate of sedimentation of particles in the liquid sample, flocculant addition means to add flocculant to the body of liquid from which the sample was drawn and means to control the addition of flocculent from the flocculant addition means into the body of liquid in accordance with the rate of sedimentation of the particles in the liquid sample, the device being characterized in that the inlet duct includes an S-bend having a lower bight portion below a lower end of the sample container and an upper bright portion adjacent to or above the upper end of the sample container, a gas inlet duct in communication with the inlet duct, valve means in the gas inlet duct to control the flow of gas through the duct, said valve means being disposed at a level adjacent to or above the upper end of the sample container, and control means to control the opening and closing of the valve means.

2. A device according to claim 1 characterized in that the gas inlet duct is in communication with the sample inlet duct at a level adjacent the level of the lower end of the container.

3. A device according to claim 1 characterized in that the means to measure the rate of sedimentation comprises a light disposed on one side of the sample container and a photoelectric cell disposed in the path of the light on the other side of the sample container.

4. A device according to claim 3 including a timer arranged to be actuated as soon as a sample reaches a desired level in the sample container and which is stopped when the particles in the container have settled to a level which allows the light to pass through the container and the liquid therein sufficiently to be registered by the photoelectric cell.

5. A device according to claim 3 including a timer arranged to be actuated as soon as a sample reaches a desired level in the sample container and which is stopped when the particles in the container have settled to a level which allows the light to pass through the container and the liquid therein sufficiently to be registered by the photoelectric cell and means to control the rate of addition of the flocculant to the body of the liquid in accordance with an algorithm based on the time recorded on the timer.

6. A device for the determination of the rate of sedimentation of particles in a sample of a liquid and controlling the addition of a flocculant to the liquid in accordance with the rate of sedimentation so determined, the device comprising a sample container, a sample inlet duct in fluid communication with the sample container and extending downwardly from a lower end thereof and adapted to extend into a body of liquid to be sampled, suction means in fluid communication with an upper end of the sample container and adapted to create a reduced pressure in the sample container such that a sample of the liquid is drawn into the sample container, means to measure a parameter indicative of the rate of sedimentation of particles in the liquid sample, flocculent addition means adapted to add flocculant to the body of liquid from which the sample was drawn, and means adapted to control the addition of flocculant from the flocculant addition means into the body of liquid in accordance with the rate of sedimentation of the particles in the liquid sample, the device being characterized in that the inlet duct includes an S-bend having a lower bight portion below a lower end of the sample container and an upper bight portion adjacent to or above the upper end of the sample container, a gas inlet duct in communication with the inlet duct at a level adjacent the level of the lower end of the container, valve means in the gas inlet duct to control the flow of gas through the duct, and control means to control the opening and closing of the valve means, and wherein the suction means and the sample container are arranged and constructed so that the reduced pressure in the sample container may be produced to draw the sample into the container up to a predetermined level, and then released when the valve means in the gas duct is opened so as to create a balanced condition such that the level in the sample container remains constant throughout the determination of the sedimentation rate.

7. A process for controlling the sedimentation of particles in a body of a liquid, said process comprising the steps of: drawing a sample of the liquid into a sample container having an upper end, and a lower end, through an inlet duct in fluid communication with the lower end of the sample container and with the body of liquid by producing a reduced pressure in the sample container, the inlet duct including an S-bend having a lower bight portion below the lower end of the sample container and an upper bight portion adjacent to or above the upper end of the sample container; opening a valve means on a gas inlet duct communicating with the S-bend to allow a gas to flow into the upper bight portion; releasing the reduced pressure in the sample container; determining a parameter representative the rate of sedimentation of particles in the sample; controlling the addition of flocculants from a flocculant addition means into the body of the liquid in accordance with the rate of sedimentation of the particles in the sample; and retaining the sample in the sample container throughout the determination of the sedimentation rate of the particles in the sample by maintaining a balance between the liquid in the sample container and the liquid remaining in the S-bend after the valve means have been opened.

* * * * *